(12) United States Patent
Tooren

(10) Patent No.: US 12,344,708 B2
(45) Date of Patent: Jul. 1, 2025

(54) TISSUE-ADHESIVE HYDROGELS

(71) Applicant: Polyganics IP B.V., Groningen (NL)

(72) Inventor: Martin Franke Tooren, Bedum (NL)

(73) Assignee: Polyganics IP B.V., Groningen (NL)

( * ) Notice: Subject to any disclaimer, the term of this patent is extended or adjusted under 35 U.S.C. 154(b) by 962 days.

(21) Appl. No.: 17/437,600

(22) PCT Filed: Mar. 11, 2020

(86) PCT No.: PCT/NL2020/050159
§ 371 (c)(1),
(2) Date: Sep. 9, 2021

(87) PCT Pub. No.: WO2020/185080
PCT Pub. Date: Sep. 17, 2020

(65) Prior Publication Data
US 2022/0185958 A1    Jun. 16, 2022

(30) Foreign Application Priority Data
Mar. 11, 2019  (NL) .................................... 2022710

(51) Int. Cl.
*C08G 65/333* (2006.01)
*A61L 24/00* (2006.01)
*A61L 24/04* (2006.01)
*C08G 69/16* (2006.01)

(52) U.S. Cl.
CPC .... *C08G 65/33327* (2013.01); *A61L 24/0031* (2013.01); *A61L 24/046* (2013.01); *C08G 69/16* (2013.01); *C08G 2210/00* (2013.01)

(58) Field of Classification Search
CPC ............................ C08G 69/16; C08G 2210/00
USPC ........................................... 564/413; 528/323
See application file for complete search history.

(56) References Cited

U.S. PATENT DOCUMENTS 5,098,999 A * 3/1992 Yamamoto ............ C07C 271/22
560/163
2008/0247984 A1  10/2008 Messersmith et al.
2022/0257837 A1* 8/2022 Loontjens .............. A01N 25/24

FOREIGN PATENT DOCUMENTS

WO       2018183284 A1   10/2018

OTHER PUBLICATIONS

Valcavi et al. "Synthesis and Antibacterial Activity of Some Ureido Cephalexin and Cefadroxil Derivatives" Il Farmaco—Ed. Sc.—vol. 35—fasc. 7. Scientifiques et medicales 1980, 563-572.

* cited by examiner

*Primary Examiner* — Fred M Teskin
(74) *Attorney, Agent, or Firm* — Banner & Witcoff, Ltd.

(57) ABSTRACT

The invention is directed to a tissue-adhesive multi-arm polymer comprising a core from which polymeric arms extent, which polymeric arms are substituted with a hydroxyl-substituted aromatic group based on compounds such as dopamine, L-DOPA, D-DOPA, tyramine, noradrenaline and/or serotonin. In addition, the invention is directed to a caprolactam blocked hydroxyl-substituted aromatic compound, suitable for the preparation of the tissue-adhesive multi-arm polymer and to the method for the preparation of the tissue-adhesive multi-arm polymer.

20 Claims, 1 Drawing Sheet

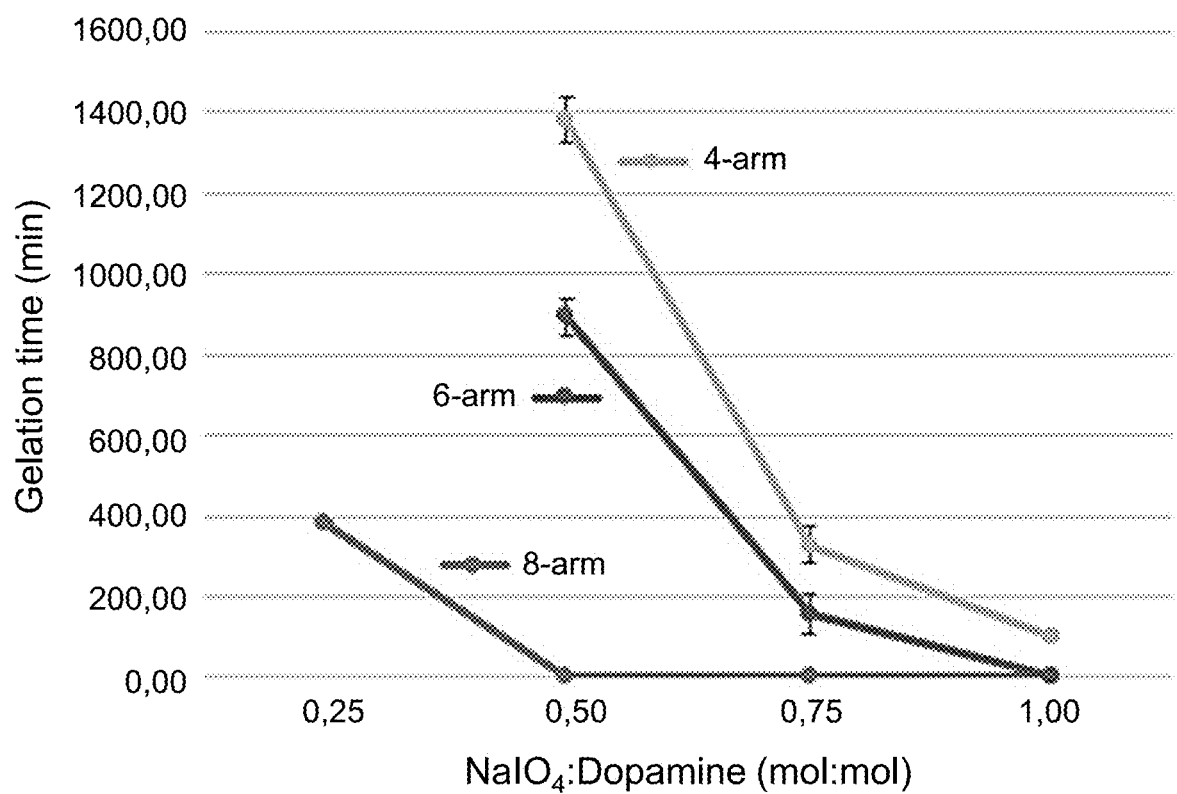

TISSUE-ADHESIVE HYDROGELS

RELATED APPLICATIONS

This application is a National Stage Application under 35 U.S.C. 371 of co-pending PCT application PCT/NL2020/050159 designating the United States and filed Mar. 11, 2020; which claims the benefit of NL application number 2022710 and filed Mar. 11, 2019, each of which are hereby incorporated by reference in their entireties.

The invention is in the field of tissue-adhesive materials. In particular, the invention is directed to tissue-adhesive multi-arm polymers and applications thereof in tissue-adhesive hydrogels. The invention is also directed to the processes to prepare the polymers and the use of a reactive intermediate in this and similar processes.

Tissue adhesives are common practice in the fields of surgery, thereby providing an alternative for the traditionally perforating materials such as sutures and staples. The currently used tissue adhesives have limited adhesive strength (e.g. fibrin-based products) or are relatively toxic (e.g. cyanoacrylate). Specific examples of known hydrogels include Evicel™, Adherus™, Tisseel/Tissucol™ and DuraSeal™, that is commercially available from Integra LifeSciences Corporation and described in e.g. U.S. Pat. No. 5,997,895. Some of the known hydrogels (e.g. DuraSeal™) are NHS-esters-based hydrogels and show a limited adhesive and burst strength. Other examples of adhesive materials are Coseal™, TissuepatchDural™, Hemopatch™ and Veriset™.

Alternatively to NHS-based gels, hydrogels have been proposed that are based on dopamine-modified poly(ethylene glycol) polymers (see Liu et al., ACS Applied Materials and Interfaces 6 (2014) 16982-16992). The polymers however, require laborious preparation, comprising NHS functionalization of poly(ethylene glycol) polymers followed by coupling with dopamine and dialysis of the dopamine and N-hydroxysuccinimide after this coupling to prevent free dopamine. Another drawback of the dopamine-modified poly(ethylene glycol) polymers by Liu is the presence of an ester bond, which limits the water resistance of these hydrogels.

Other dopamine-modified poly(ethylene glycol) polymers are disclosed in US 2008/247984 and WO 2018/183284. These documents however, also disclose elaborate, multiple-step method for preparation of these polymers.

It is desired to provide hydrogels and compounds such as polymers therefor that give a higher adhesive strength than known hydrogels and which can be prepared by less laborious methods and/or without the release of free dopamine. Further, it is desired to provide an improved method for the preparation of the polymers.

Surprisingly, the present inventors found that at least one of these objects can be met by providing a multi-arm polymer that comprises a hydroxyl-substituted aromatic group and a method for preparing the polymers using a caprolactam blocked hydroxyl-substituted aromatic compound such as a caprolactam blocked hydroxyl-substituted dopamine (CABDA). Interestingly, marine mussels adhere to substrates by spinning treads made from proteins of which are rich in the catecholic amino acid 3,4-dihydroxyphenyl alanine (DOPA). Introducing DOPA or other hydroxyl-substituted aromatics results in polymer materials that are water resistant and have good adhesive properties under wet conditions. The multi-arm facet of the polymer further results in high adhesive strength towards tissues. The caprolactam blocked hydroxyl-substituted aromatic compound provides a particular facile entry into those polymers.

Accordingly, the present invention is directed to a tissue-adhesive multi-arm polymer comprising a core from which polymeric arms extent, which polymeric arms are substituted with a hydroxyl-substituted aromatic group, and to a method for the preparation thereof.

More in particular, the invention is directed to method for preparing a tissue-adhesive multi-arm polymer having a structure according to formula I

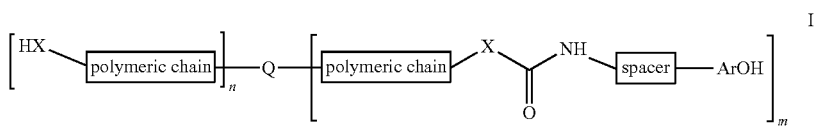

wherein Q represent a core;
the polymeric chain comprises one or more polymeric groups;
X represents O, S or NH;
the spacer represents a linear or branched $C_1$-$C_8$ hydrocarbon, optionally substituted with one or more OH, SH, halide, amide and/or carboxylate; ArOH represents an hydroxyl-substituted aromatic group;
m represents the number of functionalized polymer arms and is 2 or more, preferably 3 to 12; and
n represents the number of non-functionalized polymer arms and is a number in the range of less than m, preferably 0.

The method comprises reacting a multi-arm polymer having a structure according to formula II with the caprolactam blocked hydroxyl-substituted aromatic compound according to according to formula III, as illustrated in Scheme 1 below.

Scheme 1

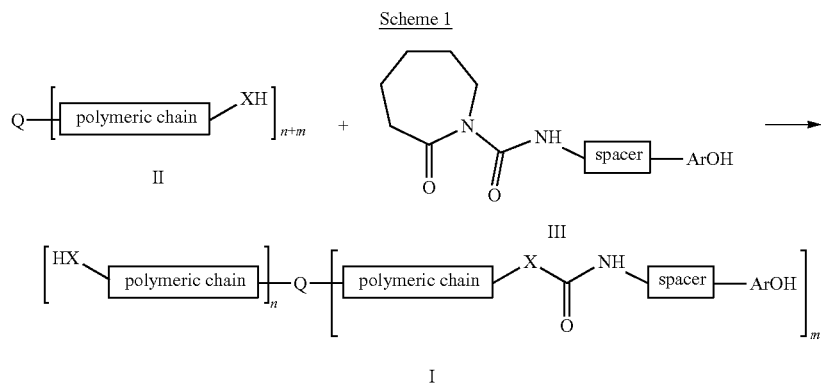

In a further aspect, the invention is directed to polymers of Formula I obtainable by said method.

Similar to what is known for DOPA, hydroxyl-substituted aromatic groups can be oxidized, after which the aromatic compound can react with tissue, typically at the ortho-position to the hydroxyl substituent. As such, the polymers and materials functionalized with hydroxyl-substituted aromatic groups can used as tissue-adhesive compounds and materials.

Particularly suitable hydroxyl-substituted aromatic groups include phenol, catechol, 3-hydroxyphenol, 4-hydroxyphenol, 2-aminophenol, 3-aminophenol, 4-aminophenol, 4-hydroxyindole, 5-hydroxyindole, 6-hydroxyindole, 7-hydroxyindole. These group are oxidizable and can subsequently react with tissue. In a preferred embodiment, the hydroxyl-substituted aromatic group is one or more selected from the group of aromatic moieties having one of the following structures:

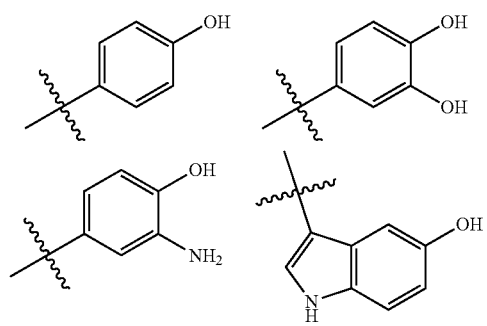

Of this group of aromatic moieties, the catechol group is particularly preferred for its presence in several naturally occurring compounds such as DOPA, dopamine, L-DOPA, R-DOPA, tyramine, noradrenaline and/or serotonin. The catechol-group is therefore generally biological well compatible and preferred for medical applications such as tissue-adhesive substances and devices. Accordingly, is a further preferred embodiment, the moiety "NH-spacer-ArOH" is based on dopamine, L-DOPA, R-DOPA, tyramine, noradrenaline and/or serotonin.

The linker in the polymer of the invention generally originates from an amine compound comprising the hydroxyl-substituted aromatic group. As will be described herein below, the functionalization of the polymer with this amine compound is also an aspect of the present invention. In the aforementioned preferred embodiment wherein the moiety "NH-spacer-ArOH" is based on dopamine, L-DOPA, R-DOPA, tyramine, noradrenaline and/or serotonin, the spacer may thus be based on $C_2$-alkylene, optionally substituted with a hydroxyl or carboxylate. Variations of this linker may however also be well possible. Esters of the carboxylate can also be applied. In general however, it is preferred to maintain a short linker, without superfluous substituents. As such, the linker is preferably a linear or branched $C_1$-$C_6$ alkylene, preferably $C_2$-$C_4$ alkylene, more preferably $C_2$ alkylene, most preferably a linear $C_2$ alkylene. The linker may optionally be substituted with an hydroxyl and/or a carboxylic acid group.

The polymer chain on which each arm of the polymer is based may be based on a variety of polymers or polymeric groups and combinations thereof. Good reaction with the tissue (i.e. good adhesion) can in particular be obtained if the tissue-adhesive polymer is based on a hydrophilic polymer. Examples of suitable hydrophilic polymers include hydrophilic polyether, polyester, poly(ester ethers), polycarbonates, polyurethanes, polyetherurethanes, polyurethane urea, poly(vinylpyrrolidone), poly(saccharide), poly(vinyl alcohol), polyoxazoline, or combinations thereof. The arms preferably comprises polyether, polyester, poly(ester ether), polyamide, polycarbonate, polyurethane or a combination thereof. The presence of a hydrophobic polymeric part is not necessarily excluded, as long as this is not detrimental to the adhesive properties of the tissue-adhesive polymer. For instance, the hydrophobic part can be overruled by a hydrophilic part of the tissue-adhesive polymer such that overall the polymer remains adhesive to tissue.

Particularly preferred polymeric chains include polyether, polyester, polycarbonate such as poly(alkylene glycol) or a poly(lactic acid), poly(caprolactone), polydioxanone, poly(glycolide) or a poly(trimethylene carbonate). Although polyesters such as poly(lactic acid) and poly(caprolactone) show favorable hydrophilic properties, the presence of the ester bonds in the polymers, in particular when combined with ethers, results in a shorter adhesion than the polyether and polycarbonate, probably due to hydrolysis of the ester bonds. Accordingly, even more preferably the polymer or polymeric group comprises poly(ethylene glycol) (PEG), polycaprolactone (PCL), poly(lactic acid) (PLA), for instance poly(L-lactic acid) (PLLA), a co-polymer of PCL and PLA or a poly(trimethylene carbonate) (PTMC), most preferably PEG.

In a particular embodiment, the tissue-adhesive multi-arm polymer has a structure according to formula Ia.

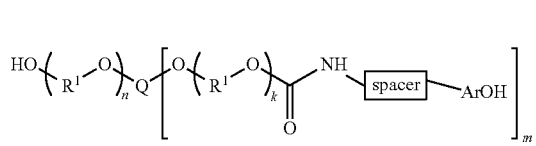

Ia

Formula Ia is a specification of formula I and Q, m and n are accordingly the same for both formulae. In formula Ia, $R^1$ represents linear or branched $C_1$-$C_4$ alkylene and/or —C(O)—$C_1$-$C_5$ alkylene; and k represents the number of polymer units of each arm and is proportional to the molecular weight of each arm. The number of polymer units of each arm k is typically in the range of 5 to 1000. For example, if the polymer is based on a multi-arm PEG weighing 40 kDa, k is about 114. Preferably k is in the range of 10 to about 250, more preferably 50 to 150 such as about 114 units.

The $R^1$ part originates from the monomeric units on which the polymer arm is based. For instance, in embodiments wherein the arm is based on poly(ethylene glycol) or poly (propylene glycol), $R^1$ represents ethylene or propylene while in embodiments wherein the arm is based on a polyester, $R^1$ represents —C(O)-alkylene, wherein —C(O)— is the carbonyl group in the polyester. In a further preferred embodiment, $R^1$ represents —C(O)—CH(CH$_3$)— (i.e. a branched —C(O)—$C_2$ alkylene originating from e.g. lactide)- or —C(O)—(CH$_2$)$_5$ (i.e. a linear —C(O)—$C_5$ alkylene originating from e.g. ε-caprolactone).

An yet another particularly preferred embodiment, the tissue-adhesive multi-arm polymer has a structure according to formula Ib.

Ib

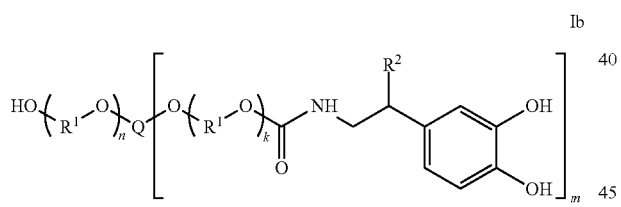

Formula Ib is a specification of formulae I and Ia and Q, m and n are accordingly the same for all formulae. The $R^1$ and k for formulae Ia and Ib are also the same. In formula Ib, $R^2$ represents H, OH, CH$_3$ or CO$_2$H or ester thereof, preferably H, and typically originates from the amine on which the hydroxyl-substituted aromatic group and spacer is based. Suitable esters of the CO$_2$H group include $C_1$-$C_6$ alkyl and aryl esters such as CO$_2$Me and CO$_2$Et.

The length of the arms can be expressed with their molecular weight. Accordingly, on average, the number-average molecular weight ($M_n$) of each arm is preferably in the range of 500 Da to 50 kDa, more preferably 1-25 kDa, most preferably 2 to 10 kDa. In addition, number-average molecular total weight of the multi-arm tissue-adhesive polymer is preferably in the range of 5 to 100 kDa, more preferably in the range of 10-80 kDa, most preferably in the range of 20-60 kDa. For instance, very good results were obtained with an 8-armed (PEG) having a number-average molecular weight of 40.000 g/mol (i.e. 40 kDa), of which each arm is thus about 5 kDa.

The number-average molecular weight can be determined by known analytical techniques such as size exclusion chromatography (SEC) according to ASTM D5296-19 and/or matrix assisted laser desorption ionization time of flight mass spectrometry (MALDI-TOF-MS) according to ISO 10927:2018.

The multi-arm nature of the polymer can be attributed to a core. The number of functionalized arms in the polymer m depends on the selected core and the substitution degree of the arms (i.e. the ratio of functionalized arms to non-functionalized arms). In general, the core may be based on any poly-functional compound to which the polymeric chains (i.e. the arms) can suitably be connected. In a preferred embodiment, the core is based on a poly-functional compound which is an initiator in polymerization reactions. This enables that the polymeric chain may be grafted from the core. Therefore, the core is preferred based on a polyol that is suitable for initiation polymerization to form polyethers or polyesters. Examples of such polyols include ethylene glycol, glycerol (GL), pentaerythritol (P), hex-aglycerol (HG), tripentaerythritol (TP), trimethylolpropane (TMP), dipentaerythritol (DP) and combinations thereof.

As such, in a preferred embodiment, Q of formula I, Ia and Ib is based on a polyol comprising m+n hydroxyl groups, preferably Q is based on a polyol of any of structures depicted below,

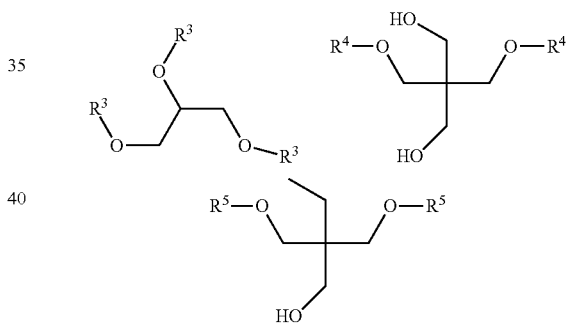

wherein each $R^3$ is individually H or

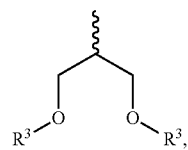

each $R^4$ is individually H or

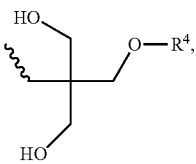

each $R^5$ is H or

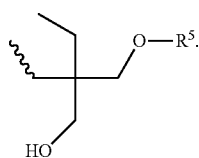

The $R^3$, $R^4$ and $R^5$ can be selected based on the amount of desired hydroxyl groups. For instance, hexaglycerol (HG) can be represented as follows.

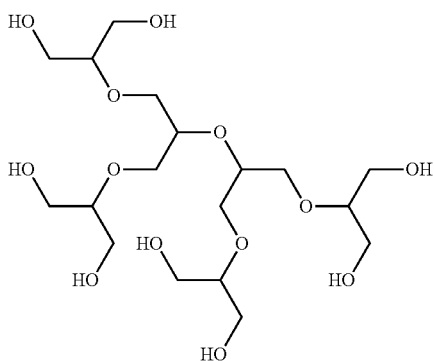 [SMILES: OCC(CO)OCC(COC(CO)CO)OC(COC(CO)CO)COC(CO)CO]

In a particular embodiment, the core is the initiator for the preparation of a multi-arm PEG, which is then used as a subsequent initiator in a polymerization reaction with lactide, trimethylenecarbonate, glycolide of caprolacton to form a multiarm block copolymer comprising a multi-arm PEG segment extended with one or more of these monomers.

In a further preferred embodiment, the number of functionalized arms m is 4 to 10, preferably 6 to 8. It was surprisingly found that gelation time decreases with an increasing m. Thus, the gelation time for the polymer wherein m is 6 is less than when m is 4, while for the polymer wherein m is 8, the gelation time is even less than when m is 6. In addition, a higher number of functionalized arms were surprisingly found to result in better adhesive properties as well as in better mechanical properties. As such, pentaerythritol (P), hexaglycerol (HG), tripentaerytritol (TP), trimethylolpropane (TMP) and dipentaerythritol (DP), in particular hexaglycerol (HG), dipentaerythritol (DP), tripentaerytritol (TP) are preferred core structures.

Generally, it is preferred that all arms are functionalized, but it may be that not all arms are substituted with the hydroxyl-substituted aromatic group, e.g. due to limitation in the method for preparation (vide infra) or by design. The substitution degree of the arms as defined by m divided by (m+n) is preferably more than 60%, more preferably more than 80%, even more preferably more than 90%, most preferably about 100%. In general, a higher substitution degree leads to better adhesion and better mechanical properties.

The substitution degree can be determined by $^1$H-NMR in combination with the following mathematical formula $$\text{substitution degree}(\%) = \frac{A}{Q \times R} \times \frac{Z \times M_n}{B \times M_w} \times 100\%$$

wherein:
A is the area of the peak or peaks corresponding to all the protons of the moiety "NH-spacer-ArOH";
Q is the number of protons in the moiety "NH-spacer-ArOH";
R is the total number of arms of the polymer;
B is the area of the peak or peaks corresponding to all the protons of polymer arms;
Z is the number of protons in the monomer on which the polymeric chain is based;
$M_w$ is the molecular weight of monomer on which the polymeric chain is based;
$M_n$ is the number-average molecular weight of the polymer without the moiety "NH-spacer-ArOH".

A further aspect of the present invention is a kit of parts comprising a first container comprising the tissue-adhesive polymer and a second container comprising an oxidizing agent. As described herein-above, the tissue-adhesive properties are obtained by oxidizing the hydroxyl-substituted aromatic group. Suitable oxidizing agents are generally known agents capable of oxidizing such groups and include periodates, peroxides, permanganates and the like, such as sodium periodate, potassium permanganate.

By mixing the contents of both containers, a hydrogel is formed that can be injected. Such a hydrogel is another aspect of the present invention.

Advantageously, the hydrogel according to the present invention demonstrates improved adhesion and/or mechanical properties vis-à-vis conventional hydrogels. The hydrogel of the present invention may have a lap shear adhesion strength of more than 0.50 N, preferably more than 0.7, more preferably more than 1, even more preferably more than 1.5, most preferably more than 2 N as determined by ASTM F2255-05.38. The burst pressure may be more than 15 mbar, preferably more than 20 mbar, more preferably more than 25 mbar as determined by ASTM F2392-04.

The tissue-adhesive polymer and the injectable hydrogel of the present invention can be used in a medical treatment of a human or animal, in particular for sealing or closing of tissue, preferably of tissue that is otherwise difficult to treat using conventional methods such applying suture, patches or staples. Due to their typical injectable nature, the polymer and hydrogel of the invention can very suitably be used in laparoscopic treatments. The polymer and hydrogel are thus well suitable for sealing the ventral cavity (including the abdominal, thoracic and pelvic cavities) like liver, lung, pancreas, spleen, bladder, kidney and/or intestine tissues.

Oxidation of the polymer may occur on-site (i.e. after appliance), before appliance, or a combination thereof (e.g. using a syringe comprising two containers corrected to a mixing section wherein the oxidation can at least partially occur).

A particular application for tissue-adhesive polymer and hydrogel is the sealing of dura mater or spinal tissue. Dura mater is the outermost membrane layer that surrounds the brain and spinal cord of the central nervous system. After e.g. trauma or cranial surgery, opened dura mater needs to be sealed to prevent leakage of cerebrospinal fluid. Even when in an operation dura mater is closed by suture, staples and such, cerebrospinal fluid may still leak, in particular through remaining small openings. It is therefore typically required that the dura mater is sealed by a surgical sealant, which preferably, is based on a tissue-adhesive material such that no glue or other type of adhesive is required to apply the sealant and seal the dura mater. Inter alia for these reasons, tissue-adhesive polymer and hydrogel in accordance with the invention is very suitable for use in methods of surgery.

Yet a further aspect of the invention is directed to the preparation of the tissue-adhesive polymer. The present inventors found that the polymer can efficiently be prepared by reacting the non-functionalized multi-arm polymer with a caprolactam blocked isocyanate derivative of the "spacer-ArOH" moiety (herein abbreviated as CAB-ArOH). Advantageously, in contrast to Liu et al., ACS Applied Materials and Interfaces 6 (2014) 16982-16992, the present tissue-adhesive polymer can be prepared without the requirement of dialysis or other elaborate and/or cumbersome purification method.

The present inventors found that CAB-ArOH can be a suitable substitute for isocyanates and offers several advantages. Isocyanates are generally toxic and there is a possibility for incomplete reactions. Furthermore, undesired crosslinking may take place in the presence of moisture and/or elevated temperatures. In contrast, the CAB-ArOH is non-toxic and stable up to a temperature of 100° C. or more.

Accordingly, a particular aspect of the invention is the preparation of the tissue-adhesive multi-arm polymer of formula I, said method comprising reacting the multi-arm polymer having a structure according to formula II with the caprolactam blocked hydroxyl-substituted aromatic (herein abbreviated as CAB-ArOH), as illustrated in Scheme 2.

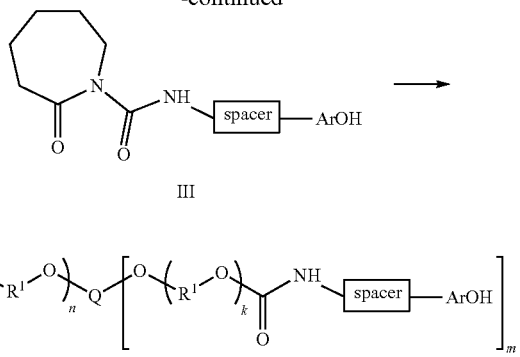

Caprolactam blocked isocyanates are known in the art and are typically used in an isocyanate-free route to urethane compounds (see e.g. Maier et al. Macromolecules (2003) 4727-4734).

In a preferred embodiment of the preparation of the tissue-adhesive multi-arm polymer, the method further comprises preparing the CAB-ArOH in a method as described herein-below.

Scheme 2

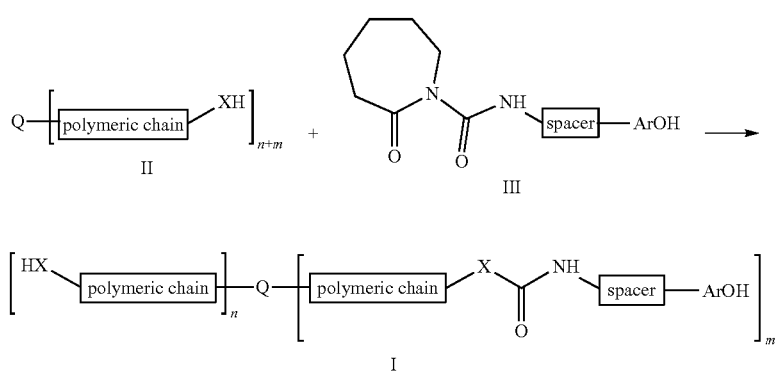

The reaction of compound II with compound III can be carried out at relatively high temperature because to the good stability of compound III. In general, the reaction temperature may be about 100 to 200° C., preferably between 130 to 180° such as about 145° C. Full conversion of compound II is then typically obtained in 8 to 24 hours, for instance in about 16 hours. Advantageously, the ArOH moiety remains intact and does not degrade nor interfere with the reaction.

In a preferred embodiment of the method according to the present invention, CAB-ArOH is reacted with the preferred embodiment of the multi-arm polymer according to formula IIa. This results in the formation of the tissue-adhesive multi-arm polymer of formula Ia, as illustrated in Scheme 3.

Scheme 3

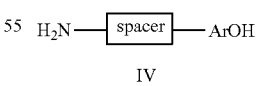

The CAB-ArOH can be readily prepared by a reaction of the compound $NH_2$-spacer-ArOH (compound IV) with carbonylbiscaprolactam (CBC, or compound V), as illustrated in Scheme 4. This reaction is preferably carried out in the presence of a base such as an organic amine (e.g. triethyl amine).

Scheme 4

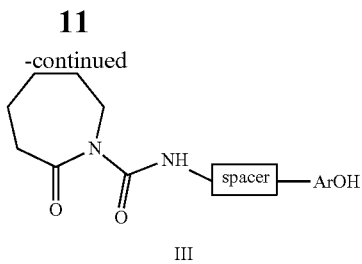

III

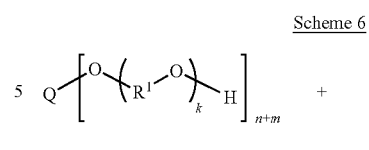

IIa

Surprisingly, conditions for the preparation of caprolactam blocked isocyanates of primary amines reported in Maier et al. Macromolecules (2003) 4727-4734 (CHCl$_3$, 75° C. for 4 hour) did not result in a good yield of the product. It was found that preferably, compound IV is used in excess vis-à-vis CBC (e.g. more than 1.3 molar equivalents such as 1.5 molar equivalents or more). The base is preferably present in an amount of more than 2 molar equivalents with respect to CBC, more preferably 3 molar equivalents or more, especially when compound IV is introduced in the reaction as a salt (e.g. a HCl salt). In addition, it is preferred that compound IV and CBC are reacted at a temperature of more than 80° C., more preferably 90° C. or more. Typical reaction times range from 8 hours to 14 days, for instance 1 to 12 days and is generally about 7 days.

Advantageously, the hydroxyl substituent at the ArOH moiety does not require a protective group as a chemoselective reaction between the amine and CBC can be obtained.

Specific examples of NH$_2$-spacer-ArOH are dopamine, L-DOPA, D-DOPA, tyramine, noradrenaline and serotonin. In preferred embodiments of the present invention as described, CBC is reacted with dopamine, L-DOPA or noradrenaline (compound IVb, wherein R$^2$ is respectively H, CO$_2$H or OH), as illustrated in Scheme 5.

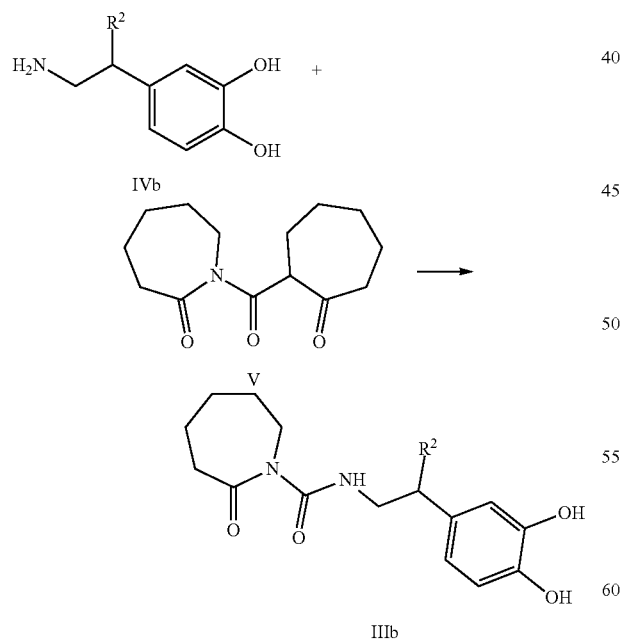

It may be appreciated that in a preferred embodiment, compound IIIb is reacted with the multi-arm polymer of formula IIa, to provide the tissue-adhesive multi-arm polymer of formula Ib, as illustrated in Scheme 6.

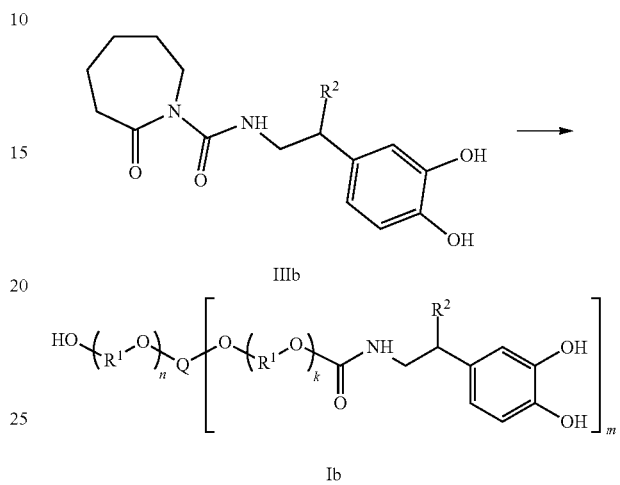

The CAB-ArOH may further be used to functionalize materials, which is yet another aspect of the present invention. Typically, such materials require reactive groups to be able to react with the CAB-ArOH. Examples of reactive groups are hydroxyl, sulfhydryl and amine reactive groups. Certain materials (e.g. cellulose) may intrinsically comprise one of more reactive groups, while other typically of materials (e.g. polyesters, polyamide, polyethers, polyurethanes, polyolefins and the like) may require activation (e.g. hydrolysis, aminolysis or electron-beam treatment).

Accordingly, the invention is further directed to a method of functionalizing an activated material A, which surface comprises at least one hydroxyl, sulfhydryl and/or amine reactive group, with a catechol derivative, said method comprising contacting said activated material A with the caprolactam blocked hydroxyl-substituted aromatic compound to provide functional material B, as illustrated in Scheme 7 wherein XH is the hydroxyl, sulfhydryl and/or amine reactive group.

-continued

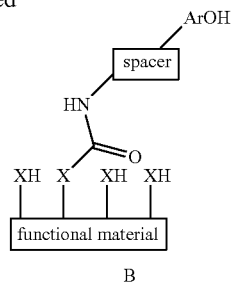

B

Examples of materials that can be functionalized in accordance with this method are the polyurethane foams, sheets and materials as for instance described in WO 99/64491 (Biomedical PUs), WO 2004/062704 (Nasal Sponge) WO 2017/171549 (Duraseal) and PCT/NL2018/050649 (Liver sealant), which are all incorporated herein in their entirety.

Accordingly, in a preferred embodiment, the functional material of the present invention comprises a foam structure, a sheet structure, a gel-like structure or combinations thereof.

As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features.

For the purpose of clarity and a concise description features are described herein as part of the same or separate embodiments, however, it will be appreciated that the scope of the invention may include embodiments having combinations of all or some of the features described.

The invention can be further illustrated by the following non-limiting examples.

BRIEF DESCRIPTION OF THE DRAWINGS

The foregoing and other features and advantages of the present embodiments will be more fully understood from the following detailed description of illustrative embodiments taken in conjunction with the accompanying drawings in which:

FIG. 1 is a graph displaying gelation time versus the ratio of NaIO$_4$ to dopamine for polymers.

EXAMPLE 1—PREPARATION OF A CAPROLACTAM BLOCKED DOPAMINE (CABDA)

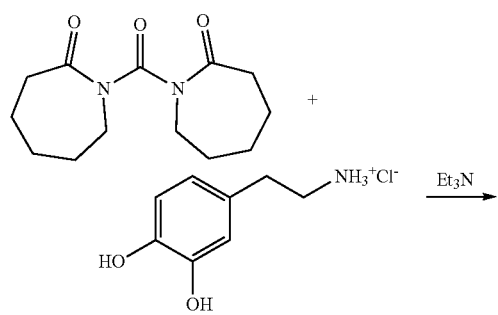

-continued

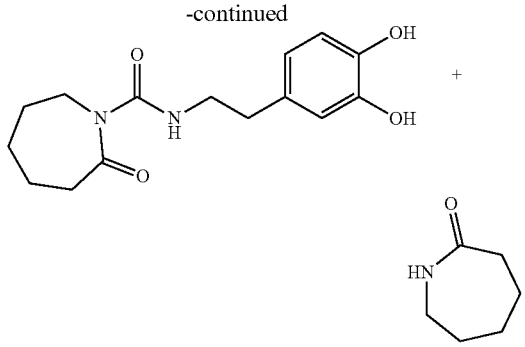

In a chloroform chloroform solution at a temperature of 90° C., dopamine hydrochloride (1.5 equivalents) and CBC were reacted in the presence of triethylamine (3 equivalents) for 48 h. CABDA was obtained in a yield of 92%.

At a round-bottom flask was added carbonyl bis caprolactam (1.0 eq; 19.82 mmol; 5.0 g) and dissolved in CHCl$_3$ (50 mL). The mixture was stirred at room temperature until dissolved, and of all times kept under inert conditions. Dopamine hydrochloride (1.5 eq; 29.73 mmol; 5.64 g) was added to the mixture and heated to 40° C. and followed by the addition of triethylamine (3.0 eq; 59.46 mmol; 6.02 g; 8.29 mL). The reaction mixture was heated to 90° C. and stirred for 48 h. The mixture was slowly cooled to room temperature. The white precipitation in the mixture was removed by Büchner filtration. The solvent was removed in vacuo, and the residue was dissolved in ethyl acetate/hexane (2/1; 90 mL). The mixture was treated with a solution of 0.5 M HCl/5% CaCl$_2$ and 5% NaCl (90 mL), 5% CaCl$_2$) (90 mL), 1M Na$_2$CO$_3$ (90 mL) and brine (90 mL). The organic layer was dried with MgSO$_4$ and filtrated. The solvents were removed in vacuo. To give a yellow solid (yield 92%).

EXAMPLE 2—FUNCTIONALIZATION OF MULTI-ARM PEG POLYMERS

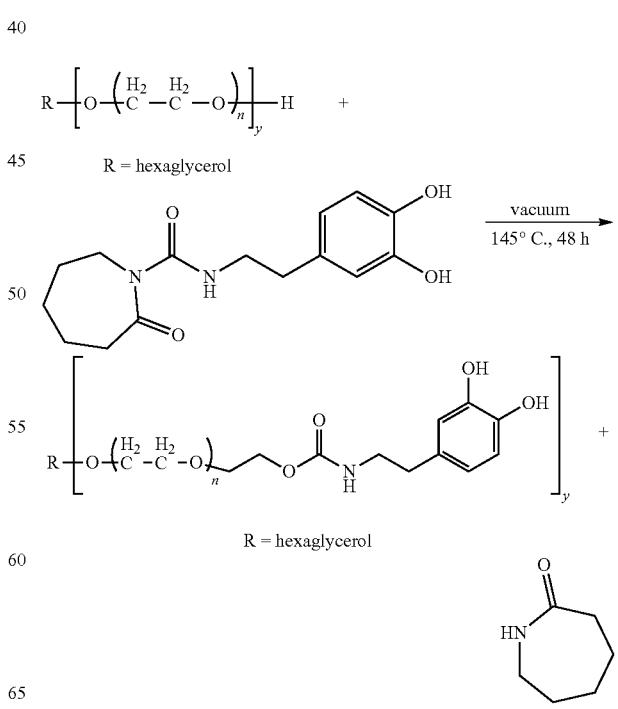

An 8-arm poly(ethylene glycol) polymer (PEG), 6-arm PEG and 4-arm PEG, having a molecular weight of 40 kDa, 30 kDa and 20 kDa respectively (8-arm-PEG40k, 6-arm-PEG30k and 4-arm-PEG20k respectively) were separately reacted with CABDA (1 equiv.) at 145° C. for 48 h under vacuum. Tissue-adhesive multi-arm polymers based on multi-arm-PEG40k and dopamine 8-ArmPEG40k-DA, 6-armPEG30k-DA and 4-armPEG20k-DA were individually obtained.

EXAMPLE 3—GELATION TIME OF 8-ARMPEG40K-DA, 6-ARMPEG30K-DA AND 4-ARMPEG20K-DA

The polymers prepared according to Example 2 were mixed with $NaIO_4$ in order to oxidize the catechol hydroxyl groups. This resulted in the formation of reactive quinone moieties which gives intermolecular crosslinking or gelation. The results are depicted in FIG. 1.

It was found that faster gelation occurs for 8-ArmPEG40k-DA>6-armPEG30k-DA>4-armPEG20k-DA. In addition, faster gelation occurs with increasing relative amounts of oxidation agent $NaIO_4$.

EXAMPLE 4—LAP SHEAR ADHESION OF 8-ARMPEG40K-DA, 6-ARMPEG30K-DA AND 4-ARMPEG20K-DA

The tissue adhesive properties of the multi-arm PEG-DA polymers prepared according to Example 2 were determined on porcine dura mater. Lap shear adhesion test were carried out according to ASTM F2255-05.38. The results are depicted in Table 1 and are compared with commercially available DuraSeal™. Results show that the lap shear strength of the 8-ArmPEG40k-DA is much higher than with DuraSeal™.

TABLE 1

| Tissue adhesive material | Lap shear strength (N) (n = 5) |
| --- | --- |
| 4-armPEG20k-DA | 0.00 |
| 6-armPEG30k-DA | 0.55 |
| 8-ArmPEG40k-DA | 2.28 |
| DuraSeal ™ | 0.66 |

EXAMPLE 5—IN VITRO BURST PRESSURE TEST OF 8-ARMPEG40K-DA, 6-ARMPEG30K-DA AND 4-ARMPEG20K-DA

The tissue adhesive properties of the multi-arm PEG-DA polymers prepared according to Example 2 were determined on porcine dura mater. The in vitro burst pressure test was performed according to ASTM F2392-04 (Standard Test Method for Burst Strength of Surgical Sealants). The results are depicted in Table 2 and are compared with commercially available DuraSeal™. Results show that the burst pressure of the 8-ArmPEG40k-DA is higher than commercially available DuraSeal™.

TABLE 2

| Tissue adhesive material | Burst pressure (mbar) (n = 5) |
| --- | --- |
| 4-armPEG20k-DA | 0.00 |
| 6-armPEG30k-DA | 25.4 |
| 8-ArmPEG40k-DA | 29.3 |
| DuraSeal ™ | 10.4 |

The invention claimed is:

1. A method for preparing a tissue-adhesive multi-arm polymer having a structure according to formula I

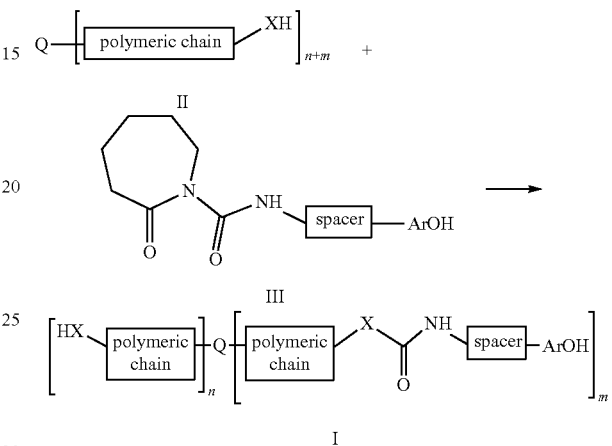

wherein Q represent a core;
the polymeric chain comprises one or more polymeric groups;
X represents O, S or NH;
the spacer represents a linear or branched $C_1$-$C_8$ hydrocarbon, optionally substituted with one or more OH, SH, halide, amide and/or carboxylate;
ArOH represents a hydroxyl-substituted aromatic group;
m represents the number of functionalized polymer arms and is 2 or more; and
n represents the number of non-functionalized polymer arms and is a number in the range of less than m, wherein said method comprises reacting a multi-arm polymer having a structure according to formula II with the caprolactam blocked hydroxyl-substituted aromatic compound according to formula III.

2. The method according to claim 1 wherein the ArOH is selected from the group consisting of phenol, catechol, 3-hydroxyphenol, 4-hydroxyphenol, 2-aminophenol, 3-aminophenol, 4-aminophenol, 4-hydroxyindole, 5-hydroxyindole, 6-hydroxyindole, 7-hydroxyindole, and combinations thereof.

3. The method according to claim 1 wherein the polymeric chain comprises polyethers, polyesters, poly(ester ethers), polyamides, polycarbonates, polyurethanes, or a combination thereof.

4. The method according to claim 1 wherein the spacer represents a linear or branched $C_1$-$C_6$ alkylene, and is optionally substituted with an hydroxyl and/or a carboxylic acid group.

5. The method according to claim 1 wherein the moiety NH-spacer-ArOH is based on dopamine, L-DOPA, D-DOPA, tyramine, noradrenaline and/or serotonin.

6. The method according to claim 1, wherein the polymeric chain is based on a polyether and/or a polyester.

7. The method according to claim 1, wherein the tissue-adhesive multi-arm polymer has a structure according to formula Ib,

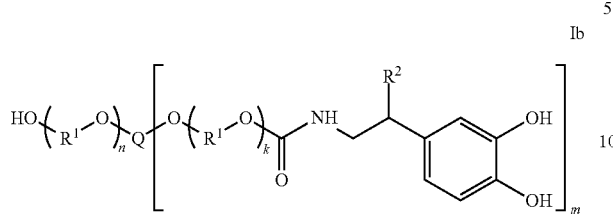

wherein Q, m and n are as defined for formula I;
$R^1$ represents linear or branched $C_1$-$C_4$ alkylene and/or —C(O)—$C_1$-$C_5$ alkylene;
$R^2$ represents H, OH, $CH_3$, or $CO_2H$ or esters thereof;
k represents the number of polymer units of each arm and proportional to the molecular weight of each arm.

8. The method according to claim 1, wherein the tissue-adhesive polymer has a number-average molecular weight in the range of 500 Da to 100 kDa.

9. The method in accordance with claim 1, wherein the core is based on a polyol selected from the group consisting of ethylene glycol, glycerol (GL), pentaerythritol (P), hexaglycerol (HG), tripentaerytritol (TP), trimethylolpropane (TMP), dipentaerythritol (DP) and combinations thereof.

10. The method in accordance with claim 1, wherein m is 4 to 10.

11. The method in accordance with claim 1, wherein the tissue-adhesive polymer has a substitution degree of the arms as defined by m divided by (m+n) of more than 60% as determined by $^1$H-NMR.

12. A tissue-adhesive multi-arm polymer having a structure according to formula I, wherein Q represent a core;
the polymeric chain comprises one or more polymeric groups;
X represents O, S or NH;
the spacer represents a linear or branched $C_1$-$C_8$ hydrocarbon, optionally substituted with one or more OH, SH, halide, amide and/or carboxylate;
ArOH represents a hydroxyl-substituted aromatic group;

m represents the number of functionalized polymer arms and is 2 or more; and
n represents the number of non-functionalized polymer arms and is a number in the range of less than m,
wherein the tissue-adhesive multi-arm polymer has a number-average molecular weight of 40 kDa or more.

13. The tissue-adhesive multi-arm polymer according to claim 12, having a number-average molecular weight in the range of 40 kDa to 100 kDa, and wherein m is more than 4.

14. A kit of parts comprising a first container comprising the tissue-adhesive polymer in accordance with claim 12 and a second container comprising an oxidizing agent.

15. An injectable hydrogel, based on an oxidized tissue-adhesive polymer in accordance with claim 12, said hydrogel having a lap shear adhesion strength of more than 0.50 N as determined by ASTM F2255-05.38 and/or said hydrogel having a burst pressure of more than 15 mbar as determined by ASTM F2392-04.

16. A method for sealing or closing of a tissue using the tissue-adhesive polymer in accordance with claim 12.

17. A method for sealing or closing of a tissue using the injectable hydrogel of claim 15.

18. A caprolactam blocked hydroxyl-substituted aromatic compound having a structure according to formula IIIb

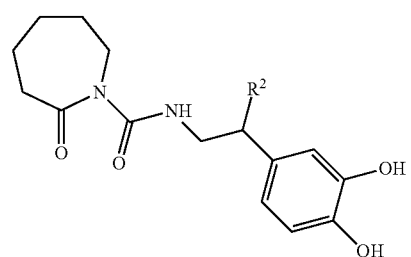

wherein $R^2$ is H, OH or $CO_2H$ or esters thereof.

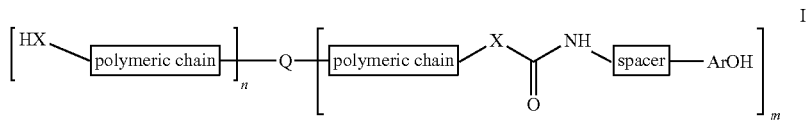

19. A method of functionalizing an activated material A, which surface comprises at least one hydroxyl, sulfhydryl and/or amine reactive group, with a catechol derivative, said method comprising contacting said activated material A with the caprolactam blocked hydroxyl-substituted aromatic compound according claim 18 provide functional material B,

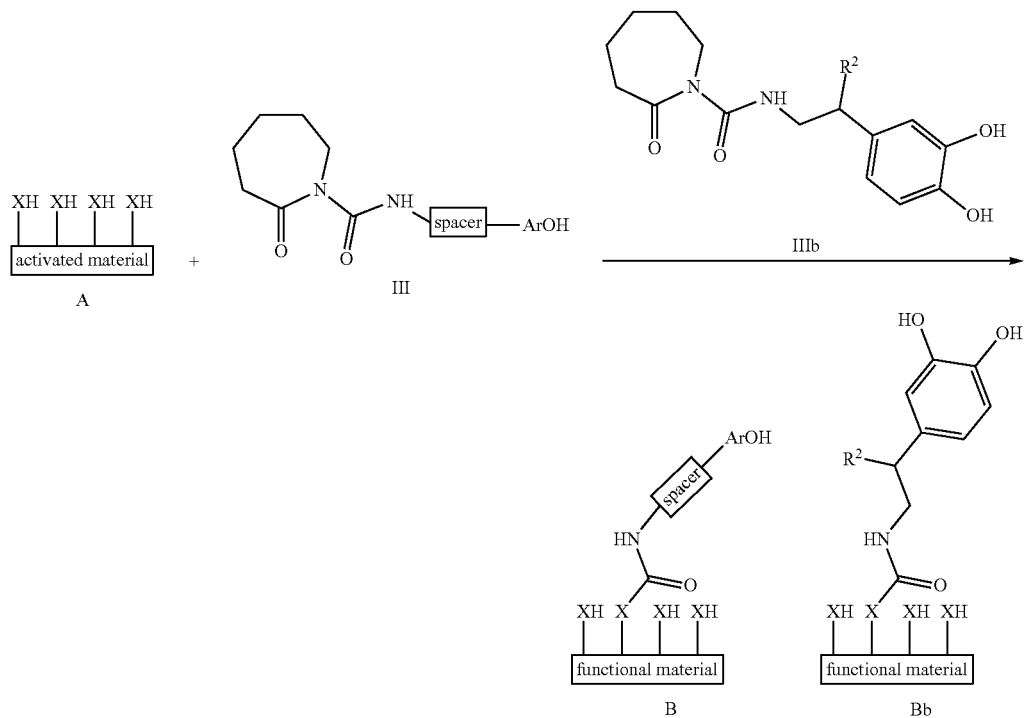

wherein XH is the hydroxyl, sulfhydryl and/or amine reactive group.

20. A functionalized material that has a foam structure, a sheet structure, a gel-like structure, or a combination thereof having a surface comprising at least one hydroxyl, sulfhydryl and/or amine reactive group of which part is functionalized with a hydroxyl-substituted aromatic compound, and wherein the functionalized material has a structure in accordance with formula Bb,

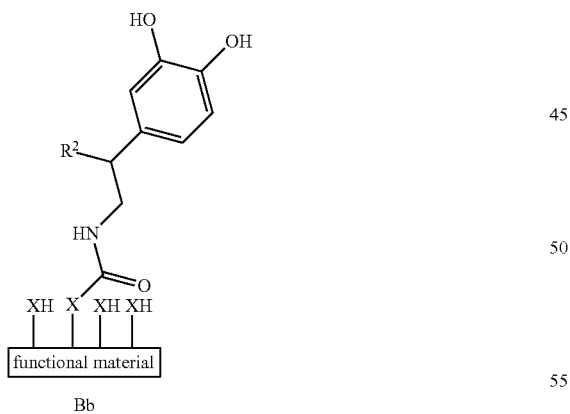

wherein XH is the hydroxyl, sulfhydryl and/or amine reactive group; and $R^2$ is H, OH or $CO_2H$ or esters thereof.

* * * * *